United States Patent
Kunihiro et al.

[11] Patent Number: 6,140,527
[45] Date of Patent: Oct. 31, 2000

[54] PROCESS FOR PRODUCING BUTYRIC ESTER DERIVATIVES

[75] Inventors: Shigeki Kunihiro, Hyogo; Fumihiko Kano, Himeji; Natsuki Mori, Kakogawa, all of Japan

[73] Assignee: Kaneka Corporation, Osaka, Japan

[21] Appl. No.: 09/355,529

[22] PCT Filed: Aug. 20, 1998

[86] PCT No.: PCT/JP98/03686

§ 371 Date: Sep. 7, 1999

§ 102(e) Date: Sep. 7, 1999

[87] PCT Pub. No.: WO99/31050

PCT Pub. Date: Jun. 24, 1999

[30] Foreign Application Priority Data

Dec. 12, 1997 [JP] Japan .................................. 9-362821

[51] Int. Cl.$^7$ .................................................. C07C 253/00
[52] U.S. Cl. .......................... 558/336; 558/337; 558/342
[58] Field of Search ...................... 558/336, 337, 558/342

[56] References Cited

U.S. PATENT DOCUMENTS 5,430,171  7/1995  Mitsuhashi et al. ..................... 558/441
5,908,953  6/1999  Matsuda et al. ......................... 558/441

*Primary Examiner*—Joseph K. McKane
*Assistant Examiner*—Joseph Murray
*Attorney, Agent, or Firm*—Pollock, Vande Sande & Amernick

[57] ABSTRACT

This invention has its objects to provide a process for producing a butyric acid ester derivative of the above general formula (2) which is capable of removing various impurity byproducts whose formation cannot be avoided by the prior art technology, particularly the compound of the above general formula (1), with good efficiency.

This invention is related to a process for producing a butyric acid ester derivative of the general formula (2) which comprises treating a mixture containing a compound of the following general formula (1) with an addition reagent capable of adding itself to said ethylenic bond to thereby convert said compound of the general formula (1) to an addition product which can be easily separated from said butyric acid ester derivative of the general formula (2) and a process for producing a butyric acid ester derivative of the general formula (2) which comprises reacting a compound of the general formula (3) with a salt of prussic acid by a flow method.

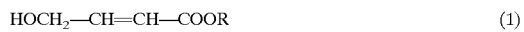

(1)

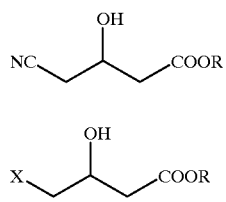

33 Claims, No Drawings

PROCESS FOR PRODUCING BUTYRIC ESTER DERIVATIVES

This application is a 371 of PCT/JP98/03686 filed Aug. 20, 1998.

FIELD OF THE INVENTION

The present invention relates to a process for producing a butyric acid ester derivative of the following general formula (2)

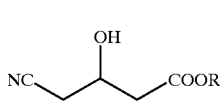

(2)

(wherein R represents a straight-chain or branched-chain alkyl group containing 1 to 4 carbon atoms).

The above butyric acid ester derivative of the general formula (2) is an important key intermediate for the production of fine chemicals, for example pharmaceuticals such as the antihyperlipidemic agent atorvastatin of the following formula (4) (Japanese Kohyo Publication Hei-7-500105) and agrochemicals.

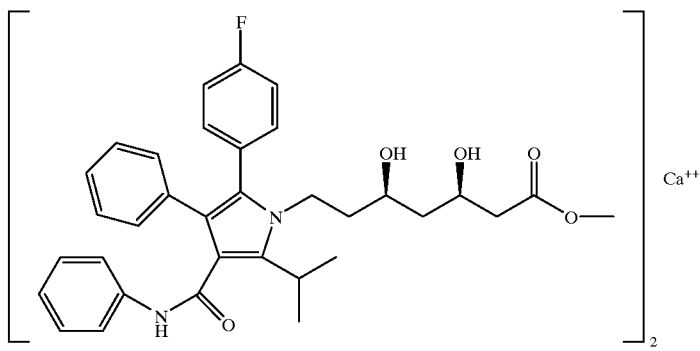

(4)

BACKGROUND OF THE INVENTION

The known technology for producing a butyric acid ester derivative of the above general formula (2) comprises reacting a compound of the following general formula (3) with a salt of prussic acid

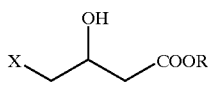

(3)

(wherein R is as defined above. X represents a group selected from the group consisting of chlorine atom, bromine atom, iodine atom, methanesulfonyloxy group, and substituted or unsubstituted phenylsulfonyloxy group).

More particularly, the typical known technology either comprises reacting ethyl 4-bromo-3-hydroxybutyrate or ethyl 4-toluenesulfonyloxy-3-hydroxybutyrate with sodium cyanide (Japanese Kohyo Publication Hei-7-500105) or comprises reacting ethyl 4-chloro-3-hydroxybutyrate, n-butyl 4-chloro-3-hydroxybutyrate or t-butyl 4-chloro-3-hydroxybutyrate with sodium cyanide (Japanese Kokai Publication Hei-5-331128).

However, the published literature referred to above are quite reticent about the impurity as a contaminant of the product derivative, a method of inhibiting formation of such impurity or a method for removing the impurity.

The inventors of the present invention scrutinized the production processes disclosed in the above published literature and found that in those known processes the by-production of a compound containing an ethylenic bond such as a compound of the following general formula (1) is inevitable and further that some impurities are formed from this byproduct containing an ethylenic bond as a precursor.

$$HOCH_2—CH=CH—COOR \qquad (1)$$

(wherein R is as defined hereinbefore)

Furthermore, the routine purification techniques such as extraction, washing, distillation and crystallization are not efficient enough to remove the above compound containing an ethylenic bond but involve a large purification loss of the butyric ester derivative of the general formula (2), etc. Therefore, as the inventors found that, even if the commercially feasible ordinary isolation and purification procedures described in the above literature are followed, it is difficult to provide the objective butyric acid ester derivative of the general formula (2) in high yield, economically and in a sufficiently high quality grade suitable for use as an intermediate in the production of fine chemicals such as pharmaceuticals and agrochemicals.

Furthermore, the reaction between said compound of the general formula (3) and said salt of prussic acid is a rather violent exothermic reaction and, therefore, although the batch process comprising charging a reactor with the total amounts of both reactants, i.e. said compound of the general formula(3) and salt of prussic acid, in one operation and reacting them at a controlled reaction temperature is feasible on a small laboratory scale because of the ease of heat removal, it is not the case with a commercial production run in which the reaction temperature can hardly be controlled because of the rapid temperature build-up of the reaction system due to the heat of reaction and, moreover, the occasional bumping of the reaction mixture makes it difficult to safely and commercially conduct this reaction involving the use of a salt of prussic acid which is highly toxic. In addition, the semi-batch process which comprises charging a reactor with either the compound of the general formula(3) or the salt of prussic acid in advance of the other, setting the reaction temperature at the necessary level and then feeding the other reactant gradually makes it possible to control the rate of heat evolution and, hence, conduct the reaction with the reaction temperature being appropriately controlled but, to anybody's surprise, it has been discovered that the reaction yield will be low even compared with the batch process on a laboratory scale.

Thus, neither a process for producing a butyric acid ester derivative of the general formula (2) with suppressed formation of said impurity nor an efficient purification procedure for removing said impurity from the product butyric acid ester derivative of the general formula (2) was known to this day and, it has heretofore been extremely difficult to produce said butyric acid ester derivative of the general formula (2) in a high quality grade either free of said impurity or containing only a minimum of impurity in high yield, economically and expediently on a commercial scale.

DETAILED DESCRIPTION OF THE INVENTION

In the above state of the art, the present invention has for its object to provide a process for producing a butyric acid ester derivative of the above general formula (2) which is capable of removing various impurity byproducts whose formation cannot be avoided by the prior art technology, particularly the compound of the above general formula (1), with good efficiency. Another object of the invention is to provide a process for producing a butyric acid ester derivative of the general formula (2), which is expedient, economical, promising a high product yield, and highly productive.

This invention provides a process for producing a butyric acid ester derivative of the general formula (2) which comprises treating a mixture containing a compound of the following general formula (1)

(wherein R represents a straight-chain or branched-chain alkyl group containing 1 to 4 carbon atoms) as an impurity and a butyric acid ester derivative of the general formula (2)

(2)

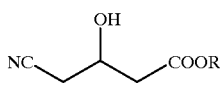

(wherein R is as defined above) as a major component with an addition reagent capable of adding itself to an ethylenic bond to thereby convert said compound of the general formula (1) to an addition product which can be separated from said butyric acid ester derivative of the general formula (2).

The present invention is now described in detail.

The process for producing a butyric acid ester derivative according to the present invention comprises treating a mixture containing said compound of the general formula (1) as an impurity and said butyric acid ester derivative of the general formula (2) as a major component with a specified addition reagent and recovering the butyric acid ester derivative of the general formula (2) in a high quality grade from said mixture expediently, economically, in high yield, and with high productivity.

The mixture mentioned above is not particularly restricted provided that it contains a compound of the above general formula (1) as an impurity and a butyric acid ester derivative of the above general formula (2) as a major component, thus including but not limited to the butyric acid ester derivative (2) provided as a purified preparation such as a distillate or a crystalline lyophilizate; the butyric acid ester derivative (2) provided as a crude preparation such as a concentrate; and the butyric acid ester derivative (2) as provided as a solution such as the reaction mixture available in the production of the derivative or a solvent extract thereof.

The butyric acid ester derivative of the general formula (2) as the major component of said mixture is not particularly restricted but includes methyl 4-cyano-3-hydroxybutyrate, ethyl 4-cyano-3-hydroxybutyrate, n-propyl 4-cyano-3-hydroxybutyrate, i-propyl 4-cyano-3-hydroxybutyrate, n-butyl 4-cyano-3-hydroxybutyrate, i-butyl 4-cyano-3-hydroxybutyrate, s-butyl 4-cyano-3-hydroxybutyrate, and t-butyl 4-cyano-3-hydroxybutyrate, among others. The butyric acid ester derivative may have its hydroxyl group protected by an alkyl, acyl or other protective group.

The addition reagent mentioned above is a reagent capable of adding itself to an ethylenic bond to convert said compound of the general formula (1) to an addition product, such as a water-soluble addition compound, which can be easily separated from said butyric acid ester derivative of the general formula (2).

The addition reagent mentioned above is not particularly restricted but includes salts of sulfurous acid such as lithium sulfite, sodium sulfite, potassium sulfite, sodium hydrosulfite, potassium hydrosulfite, calcium sulfite, magnesium sulfite and ammonium sulfite, among others. Those salts of sulfurous acid can be used each alone or in a combination of two or more species. Among the compounds mentioned above, sodium sulfite or potassium sulfite is preferred from the standpoint of cost, commercial availability, and effect of treatment.

When a sulfite is used as said addition reagent, the sulfite forms an addition product with a compound of the above general formula (1), for example, a compound of the following general formula (5);

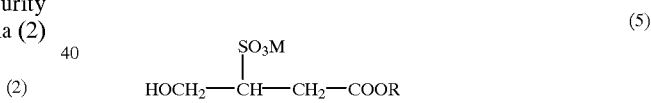

(wherein R represents a hydrogen atom, a cation species present in the system, or a straight-chain or branched-chain alkyl group containing 1 to 4 carbon atoms; M represents a hydrogen atom or a cation species present in the system). The above addition product of the general formula (5) is much different from the butyric acid ester derivative of the general formula (2) in water solubility, boiling point and other physicochemical properties so that it can be removed from said mixture with great ease and high efficiency by the expedient routine industrial purification procedures such as solvent extraction, washing, distillation and so forth.

The amount to be used of said addition reagent can be judiciously selected in consideration of the amount of the compound of the general formula (1) and the species of addition reagent, among other conditions, but it is sufficient to use an equimolar amount or an excess, preferably 1 to 10 molar equivalents, of the reagent relative to the compound of the general formula (1).

The treatment of said mixture with such an addition reagent can be carried out by mixing said addition reagent with said mixture. This mixing is preferably carried out in a solvent.

The solvent mentioned just above may be water or an organic solvent. This organic solvent is not particularly restricted but includes alcohols such as methanol, ethanol, n-propyl alcohol, isopropyl alcohol, ethylene glycol, methoxyethanol, etc.; hydrocarbons such as benzene, toluene, cyclohexane, etc.; ethers such as diethyl ether, tetrahydrofuran, dioxane, methyl t-butyl ether, dimethoxyethane, etc.; esters such as ethyl acetate, butyl acetate, etc.; halogenated hydrocarbons such as methylene chloride, chloroform, etc.; ketones such as acetone, methyl ethyl ketone, etc.; nitrogen-containing organic solvents such as dimethylformamide, acetamide, formamide, acetonitrile, etc.; and sulfur-containing organic solvents such as dimethyl sulfoxide, among others. Water and those organic solvents may be used each alone or in combination. It is, however, preferable to use either a mixed solvent consisting of one or more organic solvents and water or water alone. The still more preferred is a mixed solvent consisting of one or more organic solvents and water.

The amount to be used of said solvent can be judiciously selected in consideration of the species and amount of said addition reagent and the kind of solvent to be used.

The conditions of treatment with said addition reagent are dependent upon the species and amount of said addition reagent and the treating temperature and time selected and the treatment under strongly acidic or strongly basic conditions is not recommended because the butyric acid ester derivative of the general formula (2) will then be liable to undergo side reactions such as solvolysis or hydrolysis and transesterification. From this point of view, when a mixed solvent consisting of an organic solvent and water or water alone is used as said solvent, the pH of the system for treatment with said addition reagent is generally pH 1 to 12, preferably pH 2 to 11, more preferably pH 3 to 10, and especially pH 4 to 9.

The temperature for treatment with said addition reagent can be judiciously selected according to the desired treatment time and other factors within the range of the solidifying point through the boiling point of the treatment system but is generally 0 to 100° C. and preferably a temperature around room temperature to 90° C.

While the course of treatment with said addition reagent can be monitored by gas chromatography or high-performance liquid chromatography, the treatment time is generally 5 minutes to 4 hours in the case where, for example, the treatment is carried out within the preferred temperature range of room temperature to 90° C.

In order to suppress side reactions such as oxidation as much as possible, the treatment with said addition reagent is preferably carried out in an inert gas atmosphere such as a nitrogen atmosphere.

Upon completion of the above treatment with said addition reagent, the treated mixture is purified by using one or a suitable combination of routine purification procedures such as solvent extraction, washing, concentration, crystallization and distillation, whereby the compound of the general formula (1) is removed in the form of an addition product to said addition reagent so that the butyric acid ester derivative of the general formula (2) in a high quality grade can be provided. In carrying out this process, it is preferable to avoid using conditions under which said addition product would be easily decomposed.

In the present invention, where the butyric acid ester derivative of the general formula (2) as the major component of said mixture is an optically active compound, the butyric acid ester derivative of the general formula (2) available upon treatment with said addition reagent is also an optically active compound.

The present invention is further directed to a process for producing a butyric acid ester derivative of the general formula (2) which comprises reacting a compound of the general formula (3)

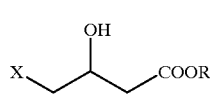

(3)

(wherein R represents a straight-chain or branched-chain alkyl group containing 1 to 4 carbon atoms; X represents a group selected from the group consisting of chlorine atom, bromine atom, iodine atom, methanesulfonyloxy group, and substituted or unsubstituted phenylsulfonyloxy group) with a salt of prussic acid in the presence of an addition reagent capable of adding itself to an ethylenic bond to convert said compound of the general formula (1) to an addition product which can be separated from said butyric acid ester derivative of the general formula (2).

Thus, in producing the butyric acid ester derivative of the general formula (2) by the reaction between said compound of the general formula (3) and said salt of prussic acid, when said reaction is conducted in the presence of said addition reagent, the butyric acid ester derivative of the general formula (2) in a high quality grade is obtained.

The compound of the general formula (3) is not particularly restricted but includes methyl 4-chloro-3-hydroxybutyrate, ethyl 4-chloro-3-hydroxybutyrate, n-propyl 4-chloro-3-hydroxybutyrate, i-propyl 4-chloro-3-hydroxybutyrate, n-butyl 4-chloro-3-hydroxybutyrate, i-butyl 4-chloro-3-hydroxybutyrate, s-butyl 4-chloro-3-hydroxybutyrate, t-butyl 4-chloro-3-hydroxybutyrate, methyl 4-bromo-3-hydroxybutyrate, ethyl 4-bromo-3-hydroxybutyrate, n-propyl 4-bromo-3-hydroxybutyrate, i-propyl 4-bromo-3-hydroxybutyrate, n-butyl 4-bromo-3-hydroxybutyrate, i-butyl 4-bromo-3-hydroxybutyrate, s-butyl 4-bromo-3-hydroxybutyrate, t-butyl 4-bromo-3-hydroxybutyrate, methyl 4-iodo-3-hydroxybutyrate, ethyl 4-iodo-3-hydroxybutyrate, n-propyl 4-iodo-3-hydroxybutyrate, i-propyl 4-iodo-3-hydroxybutyrate, n-butyl 4-iodo-3-hydroxybutyrate, i-butyl 4-iodo-3-hydroxybutyrate, s-butyl 4-iodo-3-hydroxybutyrate, t-butyl 4-iodo-3-hydroxybutyrate, methyl 4-methanesulfonyloxy-3-hydroxybutyrate, ethyl 4-methanesulfonyloxy-3-hydroxybutyrate and n-propyl 4-methanesulfonyloxy-3-hydroxybutyrate, among others.

There may also be mentioned
i-propyl 4-methanesulfonyloxy-3-hydroxybutyrate,
n-butyl 4-methanesulfonyloxy-3-hydroxybutyrate,
i-butyl 4-methanesulfonyloxy-3-hydroxybutyrate,
s-butyl 4-methanesulfonyloxy-3-hydroxybutyrate,
t-butyl 4-methanesulfonyloxy-3-hydroxybutyrate,
methyl 4-phenylsulfonyloxy-3-hydroxybutyrate,
ethyl 4-phenylsulfonyloxy-3-hydroxybutyrate,
n-propyl 4-phenylsulfonyloxy-3-hydroxybutyrate,
i-propyl 4-phenylsulfonyloxy-3-hydroxybutyrate,
n-butyl 4-phenylsulfonyloxy-3-hydroxybutyrate,
i-butyl 4-phenylsulfonyloxy-3-hydroxybutyrate,
s-butyl 4-phenylsulfonyloxy-3-hydroxybutyrate,
t-butyl 4-phenylsulfonyloxy-3-hydroxybutyrate,
methyl 4-toluenesulfonyloxy-3-hydroxybutyrate,
ethyl 4-toluenesulfonyloxy-3-hydroxybutyrate,
n-propyl 4-toluenesulfonyloxy-3-hydroxybutyrate,
i-propyl 4-toluenesulfonyloxy-3-hydroxybutyrate,
n-butyl 4-toluenesulfonyloxy-3-hydroxybutyrate,
i-butyl 4-toluenesulfonyloxy-3-hydroxybutyrate,
s-butyl 4-toluenesulfonyloxy-3-hydroxybutyrate,
t-butyl 4-toluenesulfonyloxy-3-hydroxybutyrate, among others.

Among them, the compounds preferred from the standpoint of cost and industrial availability are methyl 4-chloro-3-hydroxybutyrate, ethyl 4-chloro-3-hydroxybutyrate, n-propyl 4-chloro-3-hydroxybutyrate, i-propyl 4-chloro-3-hydroxybutyrate, n-butyl 4-chloro-3-hydroxybutyrate, i-butyl 4-chloro-3-hydroxybutyrate, s-butyl 4-chloro-3-hydroxybutyrate, t-butyl 4-chloro-3-hydroxybutyrate, methyl 4-bromo-3-hydroxybutyrate, ethyl 4-bromo-3-hydroxybutyrate, n-propyl 4-bromo-3-hydroxybutyrate, i-propyl 4-bromo-3-hydroxybutyrate, n-butyl 4-bromo-3-hydroxybutyrate, i-butyl 4-bromo-3-hydroxybutyrate, s-butyl 4-bromo-3-hydroxybutyrate and t-butyl 4-bromo-3-hydroxybutyrate. The still more preferred are methyl 4-chloro-3-hydroxybutyrate, ethyl 4-chloro-3-hydroxybutyrate, t-butyl 4-chloro-3-hydroxybutyrate, methyl 4-bromo-3-hydroxybutyrate, ethyl 4-bromo-3-hydroxybutyrate and t-butyl 4-bromo-3-hydroxybutyrate. The particularly preferred are ethyl 4-chloro-3-hydroxybutyrate and ethyl 4-bromo-3-hydroxybutyrate.

The above compound of the general formula (3) can be produced typically by carboalkoxylation of the corresponding epihalohydrin as described in Journal of Organic Chemistry 32, 3888 (1967), by chemical or enzymatic reduction of the corresponding β-keto ester as described in Tetrahedron Letters 35, No. 44, 8119 (1994) and Japanese Kokai Publication Sho-64-60391, or by sulfonylation of the corresponding β, γ-dihydroxy ester as described in Japanese Kohyo Publication Hei-7-500105.

The salt of prussic acid mentioned above is not particularly restricted but includes salts of prussic acid with inorganic bases, such as sodium cyanide, potassium cyanide, etc.; and salts of prussic acid with organic bases such as amines. Those salts of prussic acid can be used each alone or in a combination of two or more species. From the standpoint of cost and industrial availability, salts of prussic acid with inorganic bases are preferred and it is particularly advantageous to use sodium cyanide or potassium cyanide.

The amount to be used of said salt of prussic acid is not particularly restricted but is preferably 1 to 2 equivalents based on the amount of said compound of the general formula (3). The more preferred range is 1 to 1.5 equivalents and the still more preferred range is 1.1 to 1.4 equivalents.

The amount to be used of said addition reagent can be judiciously selected in consideration of the species of addition reagent selected and the like, but is preferably 0.01 to 1 mole relative to each mole of said compound of the general formula (3). The still more preferred range is 0.1 to 0.5 mole.

The reaction between said compound of the general formula (3) and said salt of prussic acid in the presence of said addition reagent is carried out by admixing said compound of the general formula (3), said salt of prussic acid and said addition reagent together. This admixing is preferably carried out in a solvent.

The solvent mentioned above may be water or an organic solvent. This organic solvent is not particularly restricted but includes alcohols such as methanol, ethanol, n-propyl alcohol, isopropyl alcohol, ethylene glycol, methoxyethanol, etc.; hydrocarbons such as benzene, toluene, cyclohexane, etc.; ethers such as diethyl ether, tetrahydrofuran, dioxane, methyl t-butyl ether, dimethoxyethane, etc.; esters such as ethyl acetate, butyl acetate, etc.; halogenated hydrocarbons such as methylene chloride, chloroform, etc.; ketones such as acetone, methyl ethyl ketone, etc.; nitrogen-containing organic solvents such as dimethylformamide, acetamide, formamide, acetonitrile, etc.; and sulfur-containing organic solvents such as dimethyl sulfoxide, among others. Water and said organic solvents may be used each alone or in combination. It is, however, preferable to use either a mixed solvent consisting of one or more water-miscible organic solvents and water or water alone. The still more preferred is a mixed solvent consisting of one or more water-miscible organic solvents and water.

The amount to be used of said solvent is judiciously selected in consideration of the species and amount of the compound of the general formula (3), the species and amount of said salt of prussic acid, the species and amount of said addition reagent, and the kind of solvent to be used but should be sufficient to insure that the concentration of said compound of the general formula (3) will be preferably 1 to 100 w/v %, more preferably 10 to 50 w/v %.

The temperature for this reaction can be judiciously selected according to the desired treating time and other factors within the range from the solidifying point to the boiling point of the reaction system but is generally 0 to 100° C. and preferably a temperature around room temperature to 90° C.

The course of this reaction can be monitored by gas chromatography or high-performance liquid chromatography and in case the reaction is conduced within said preferred temperature range of about room temperature to 90° C., it is preferable to provide an aging period of 5 minutes to 4 and odd hours for the thorough conversion to said addition product following completion of the main reaction.

To minimize side reactions such as oxidation as possible, the above reaction is preferably carried out in an inert gas atmosphere such as a nitrogen atmosphere.

After completion of the reaction, the reaction mixture is subjected to any or a combination of the routine procedures such as solvent extraction, washing, concentration, crystallization and distillation, whereby the compound of the general formula (1) can be removed in the form of an addition product with said addition reagent, thus enabling isolation of the butyric acid ester derivative of the general formula (2) of high quality. In carrying out this process, it is recommendable to avoid conditions liable to induce decomposition of said addition product.

Where the compound of the general formula (3) is an optically active compound, the product butyric acid ester derivative of the general formula (2) which has a steric configuration corresponding to that of the compound of the general formula (3) can be obtained.

The present invention in another aspect is concerned with a process for producing a butyric acid ester derivative of the general formula (2) which comprises reacting a compound of the general formula (3) with a salt of prussic acid by a flow method.

Thus, in producing said butyric acid ester derivative of the general formula (2) by reacting said compound of the general formula (3) with said salt of prussic acid, the butyric acid ester derivative of the general formula (2) can be obtained in high yield by conducting the above reaction by a flow method.

The reaction between said compound of the general formula (3) and said salt of prussic acid involves evolution of a large quantity of heat so that usually the temperature of the reaction system can hardly be controlled but this temperature control is made feasible when the reaction is carried out by a flow method.

This reaction by a flow method is preferably carried out using a tubular reactor, a thin-film reactor or a series of continuous stirred tank reactor. Those reactors are preferred because of the relatively high heat-exchange capacity compared with the tank reactor equipped with an agitator which is conventionally used for batch or semi-batch reactions.

The reaction by said flow method is carried out by feeding said compound of the general formula (3) and salt of prussic acid into a reactor as parallel flow to mix them in the reactor or mixing said compound of the general formula (3) with said salt of prussic acid either ahead of time or extemporaneously to charge the mixture into a reactor. In this operation, the mixing and reaction are preferably carried out in a solvent.

Referring to the above reaction by a flow method, the flow rate of the reaction mixture can be judiciously selected according to the species and amount of said compound of the general formula (3), the species and amount of said salt of prussic acid, the type and amount of solvent used, and the reaction temperature, among other conditions. Usually, the flow rate can be set so that the residence time during the reaction mixture is passed through the reactor once will be equal to, or longer than, the time necessary for completion of the reaction. It may also be so arranged that the reaction mixture is passed through the reactor a plurality of times and that the total of residence times will be at least equal to the time necessary for completion of the reaction.

Referring to the above reaction by a flow method, the type and amount of solvent, reaction temperature, and the species and amount of said salt of prussic acid, and the procedure for separation of the addition product after the reaction may be similar to conditions of the reaction between the compound of the general formula (3) and the salt of prussic acid in the presence of said addition reagent which has already been described in detail. Similarly, where the compound of the general formula (3) is an optically active compound, the butyric acid ester derivative of the general formula (2) which has a steric configuration corresponding to that of the compound of the general formula (3) can be obtained.

By conducting the above reaction by a flow method in the presence of said addition reagent, the butyric acid ester derivative of the general formula (2) containing a minimum of the impurity compound of the general formula (1) can be obtained in high yield.

The amount of said addition reagent can be judiciously selected according to the amount of said compound of the general formula (1) and the species of addition reagent but is preferably 0.01 to 1 molar equivalent, more preferably 0.1 to 0.5 molar equivalent, based on the amount of the compound of the general formula (3).

The reaction by said flow method in the presence of said addition reagent is carried out by feeding said compound of the general formula (3), said salt of prussic acid and said addition reagent into a reactor as a parallel flow and mixing them together in the reactor or mixing said compound of the general formula (3), said salt of prussic acid and said addition reagent either ahead of time or extemporaneously and charging the mixture to the reactor. In this operation, the mixing and reaction are preferably carried out in a solvent.

Of the above-described two processes, namely ① the process which comprises treating a mixture containing a compound of the general formula (1) as an impurity and a butyric acid ester derivative of the general formula (2) as a major component with an addition reagent capable of adding itself to the ethylenic bond of said compound of the general formula (1) to thereby convert compound (1) to an addition product separable from said butyric acid ester derivative of the general formula (2) (inclusive of the process which comprises reacting the compound of the general formula (3) with said salt of prussic acid in the presence of said addition reagent) and ② the process which comprises reacting said compound of the general formula (3) with said salt of prussic acid by a flow method, the former process ① can be used with advantage to provide the butyric acid ester derivative of the general formula (2) in a high quality grade with a minimum of contamination by the impurity compound of the general formula (1). On the other hand, by carrying out the latter process ②, the butyric acid ester derivative of the general formula (2) can be obtained in high yield. Furthermore, by carrying out the above process ① and process ② in a combination, the butyric acid ester derivative of the general formula (2) in a high quality grade with a minimum of contamination by the impurity compound of the general formula (1) can be provided in high yield.

BEST MODE FOR CARRYING OUT THE INVENTION

The following examples are intended to illustrate the present invention in further detail and should by no means be construed as defining the scope of the invention.

In the following examples, (R)-4-cyano-3-hydroxybutyric acid ethyl ester (the general formula (2) wherein R=ethyl) was used as the butyric acid ester derivative of the general formula (2) to be treated with an addition reagent capable of adding itself to an ethylenic bond and (S)-4-chloro-3-hydroxybutyric acid ethyl ester (the general formula (3) wherein X=chlorine atom and R=ethyl) was used as the compound of the general formula (3) to be reacted with a salt of prussic acid.

The yields and contents of ethyl 4-hydroxycrotonate (the general formula (1) wherein R=ethyl), ethyl 4-cyano-3-hydroxybutyrate and ethyl 4-chloro-3-hydroxybutyrate as mentioned in the examples were determined by the following analytical system.

High-performance liquid chromatography (HPLC):
  Apparatus: an HPLC system equipped with a UV detector
  Column packing: octylsilylated silica gel (Φ 5 μm)
  Column size: 4.6 mm×250 mm
  Mobile phase: 18 parts of acetonitrile for HPLC+82 parts of distilled water for HPLC
  Column temperature: 25±1° C.
  Flow rate: 1.0 mL/min.
  Detector: UV 205 nm
Retention time:
  Ethyl 4-hydroxycrotonate 9 to 10 min, approx.
  Ethyl 4-cyano-3-hydroxybutyrate 8 min. approx.
  Ethyl 4-chloro-3-hydroxybutyrate 15 min. approx.

EXAMPLE 1

Ethyl 4-cyano-3-hydroxybutyrate (10.6 g) containing 5.2 w/w % [relative to the ethyl 4-cyano-3-hydroxybutyrate (the same applies hereinafter)] of ethyl 4-hydroxycrotonate was mixed with 25.2 g of ethyl acetate. A 10.1 g portion of this mixture was taken and 10.2 g of water and 1.0 g of sodium sulfite were added followed by stirring at room temperature for 4 hours. Then, 3.2 g of sodium chloride was added so as to substantially saturate the water layer with NaCl.

The yield of ethyl 4-cyano-3-hydroxybutyrate in an ethyl acetate layer was 93% and the ethyl 4-hydroxycrotonate content of said layer was 0.01 w/w % (by weight relative to ethyl 4-cyano-3-hydroxybutyrate (the same applies hereinafter); rate of removal: 99.9%).
Ethyl 4-hydroxycrotonate
  $^1$H-NMR (CDCl$_3$, 400 MHz)
  σ: 1.29 (3H, t), 2.75 (1H, br), 4.20 (2H, q), 4.33 (2H, br), 6.09 (1H, m), 7.03 (1H, m)
  $^{13}$C-NMR (CDCl$_3$, 100 MHz)

σ: 14.22, 60.53, 61.81, 120.13, 147.04, 166.62

EXAMPLE 2

Using 1.1 g of potassium sulfite in lieu of 1.0 g of sodium sulfite, the procedure of Example 1 was otherwise repeated.

The yield of ethyl 4-cyano-3-hydroxybutyrate in an ethyl acetate layer was 94% and the ethyl 4-hydroxycrotonate content was 0.01 w/w % (rate of removal: 99.9%).

COMPARATIVE EXMAPLE 1

Omitting the addition of 1.0 g of sodium sulfite, the procedure of Example 1 was otherwise repeated.

The yield of ethyl 4-cyano-3-hydroxybutyrate in an ethyl acetate layer was 94% and the ethyl 4-hydroxycrotonate content was 5.5 w/w % (rate of removal: 0.6%).

EXAMPLE 3

Ten (10.0) grams of ethyl 4-chloro-3-hydroxybutyrate (purity 92%), 3.0 g of sodium cyanide, 1.4 g of sodium sulfite, 17.6 g of water and 15.0 g of formamide were mixed and stirred at 60° C. for 2 hours and the reaction mixture was allowed to cool to room temperature.

The yield of ethyl 4-cyano-3-hydroxybutyrate was 67% and the ethyl 4-hydroxycrotonate content was 0.08 w/w % (by weight relative to ethyl 4-cyano-3-hydroxybutyrate (the same applies hereinafter)).

EXAMPLE 4

Using 1.8 g of potassium sulfite in lieu of 1.4 g of sodium sulfite, the procedure of Example 3 was otherwise repeated.

The yield of ethyl 4-cyano-3-hydroxybutyrate was 66% and the ethyl 4-hydroxycrotonate content was 0.03 w/w %.

COMPARATIVE EXAMPLE 2

Omitting the addition of 1.4 g of sodium sulfite, the procedure of Example 3 was otherwise repeated.

The yield of ethyl 4-cyano-3-hydroxybutyrate was 69% and the ethyl 4-hydroxycrotonate content was 3.3 w/w %.

EXAMPLE 5

From the reaction mixture containing 3.3 w/w % of ethyl 4-hydroxycrotonate as an impurity as obtained in the procedure of Comparative Example 2, a 15.0 g portion was taken, 0.6 g of sodium sulfite was added, and the mixture was stirred at room temperature for 4 hours.

The yield of ethyl 4-cyano-3-hydroxybutyrate was 93% and the ethyl 4-hydroxycrotonate content was 0.46 w/w % (rate of removal: 85%).

EXAMPLE 6

Using 0.6 g of potassium sulfite in lieu of 0.6 g of sodium sulfite, the procedure of Example 5 was otherwise repeated.

The yield of ethyl 4-cyano-3-hydroxybutyrate was 98% and the ethyl 4-hydroxycrotonate content was 0.06 w/w % (rate of removal: 98%).

EXAMPLE 7

Under ice-cooling, 36.0 g of ethyl 4-chloro-3-hydroxybutyrate (purity 92%), 13.0 g of sodium cyanide, 32.0 g of water and 74.5 g of formamide were mixed. This mixture was immediately passed through a 5 mm (i.d.)×1 m tubular reactor controlled at a temperature of 80° C. at a flow rate of about 5 mL/min. The reaction mixture emerging from the reactor was immediately cooled with ice. With the ethyl 4-cyano-3-hydroxybutyrate content of the reaction mixture being monitored by high-performance liquid chromatography, the mixture was repeatedly passed through the tubular reactor. The yield became maximal after 8 passes.

The yield of ethyl 4-cyano-3-hydroxybutyrate was 85.0%. The ethyl 4-hydroxycrotonate content was 1.3 w/w %.

COMPARATIVE EXAMPLE 3

Thirty-six (36.0) grams of ethyl 4-chloro-3-hydroxybutyrate (purity 92%) was mixed with 74.5 g of formamide and the mixture was adjusted to 80° C. While this mixture was stirred, an aqueous solution of sodium cyanide (13.0 g in 32.0 g $H_2O$) was added dropwise over about 50 minutes. After completion of dropwise addition, the mixture was further allowed to react at 80° C. for about 1 hour.

The yield of ethyl 4-cyano-3-hydroxybutyrate was 77.5%.

COMPARATIVE EXAMPLE 4

Thirteen (13.0) grams of sodium cyanide, 74.5 g of formamide and 32.0 g of water were mixed together and adjusted to 80° C. While this mixture was stirred, 36.0 g of ethyl 4-chloro-3-hydroxybutyrate (purity 92%) was added dropwise over about 50 minutes. After completion of dropwise addition, the mixture was further allowed to react at 80° C. for about 1 hour.

The yield of ethyl 4-cyano-3-hydroxybutyrate was 55.4%.

EXAMPLE 8

Under ice-cooling, 36.0 g of ethyl 4-chloro-3-hydroxybutyrate (purity 92%), 11.0 g of sodium cyanide, 25.0 g of sodium sulfite, 21.5 g of water and 85.0 g of formamide were mixed together. This mixture was immediately passed through a 5 mm (in. dia.)×1 m tubular reactor controlled at 80° C. at a flow rate of about 5 mL/min. The emergent reaction mixture was immediately cooled with ice. With ethyl 4-cyano-3-hydroxybutyrate in the reaction mixture being monitored by high-performance liquid chromatography, the reaction mixture was repeatedly passed through the tubular reactor. The yield of ethyl 4-cyano-3-hydroxybutyrate showed a maximum value of 85.4% after the 8th pass.

The ethyl 4-hydroxycrotonate content at this point of time was 0.07 w/w %.

INDUSTRIAL APPLICABILITY

The process for producing a butyric acid ester derivative according to the present invention being as described above, it is by now possible to provide a butyric acid ester of the general formula (2) in a high quality grade with a minimum of contamination by the impurity compound of the general formula (1) in an expedient, economical and productive manner.

What is claimed is:

1. A process for producing a butyric acid ester derivative of the following general formula (2)

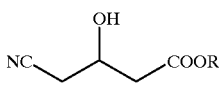 (2)

wherein R represents a straight-chain or branched-chain alkyl group containing 1 to 4 carbon atoms which comprises treating a mixture containing a compound of the following general formula (1)

 (1)

wherein R has the same meaning as defined above, as an impurity and said butyric acid ester derivative of the general formula (2) as a major component with an addition reagent capable of adding itself to an ethylenic bond to convert said compound of the general formula (1) to an addition product separable from said butyric acid ester derivative of the general formula (2).

2. The process for producing a butyric acid ester derivative according to claim 1 wherein R is ethyl or t-butyl.

3. The process for producing a butyric acid ester derivative according to claim 2 wherein R is ethyl.

4. The process for producing a butyric acid ester derivative according to claim 1, wherein the addition product is a water-soluble compound.

5. The process for producing a butyric acid ester derivative according to claim 1, wherein the addition reagent is a salt of sulfurous acid.

6. The process for producing a butyric acid ester derivative according to claim 5 wherein the addition reagent is sodium sulfite or potassium sulfite.

7. The process for producing a butyric acid ester derivative according to claim 1, wherein the butyric acid ester derivative of the general formula (2) is an optically active compound.

8. A process for producing a butyric acid ester derivative of the general formula (2)

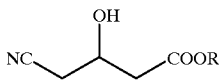 (2)

wherein R represents a straight-chain or branched-chain alkyl group containing 1 to 4 carbon atoms, which comprises reacting a compound of the general formula (3)

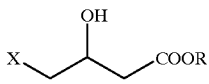 (3)

wherein R has the same meaning as defined above; X represents a group selected from the group consisting of chlorine atom, bromine atom, iodine atom, methanesulfonyloxy group, and substituted or unsubstituted phenylsulfonyloxy group, with a salt of prussic acid in the presence of an addition reagent capable of adding itself to an ethylenic bond to convert a compound of the general formula (1)

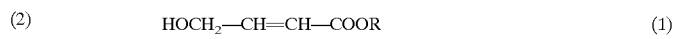 (1)

wherein R has the same meaning as defined above, to an addition product separable from said butyric acid ester derivative of the general formula (2).

9. The process for producing a butyric acid ester derivative according to claim 8 wherein R is ethyl or t-butyl.

10. The process for producing a butyric acid ester derivative according to claim 9 wherein R is ethyl.

11. The process for producing a butyric acid ester derivative according to claim 8, wherein the addition product is a water-soluble compound.

12. The process for producing a butyric acid ester derivative according to claim 8, wherein the addition reagent is a salt of sulfurous acid.

13. The process for producing a butyric acid ester derivative according to claim 12 wherein the addition reagent is sodium sulfite or potassium sulfite.

14. The process for producing a butyric acid ester derivative according to claim 8, wherein X is chlorine atom or bromine atom.

15. The process for producing a butyric acid ester derivative according to claim 14 wherein X is chlorine atom.

16. The process for producing a butyric acid ester derivative according to claim 8, wherein the salt of prussic acid is sodium cyanide or potassium cyanide.

17. The process for producing a butyric acid ester derivative according to claim 16 wherein the salt of prussic acid is sodium cyanide.

18. The process for producing a butyric acid ester derivative according to claim 8, wherein each of the compounds of the general formula (3) and the butyric acid ester derivative of the general formula (2) is an optically active compound.

19. A process for producing a butyric acid ester derivative of the general formula (2)

 (2)

wherein R represents a straight-chain or branched-chain alkyl group containing 1 to 4 carbon atoms, which comprises reacting a compound of the general formula (3)

 (3)

wherein R has the same meaning as defined above; X represents a group selected from the group consisting of chlorine atom, bromine atom, iodine atom, methanesulfonyloxy group, and substituted or unsubstituted phenylsulfonyloxy group, with a salt of prussic acid wherein the reaction is carried out by a flow method.

20. The process for producing a butyric acid ester derivative according to claim 19 wherein the reaction is carried out by the flow method using a reactor selected from the group consisting of a tubular reactor, a thin-film reactor and a series of continuous stirred tank reactors.

21. The process for producing a butyric acid ester derivative according to claim 20 wherein the tubular reactor is used as the reactor.

22. The process for producing a butyric acid ester derivative according to claim 20 wherein the thin-film reactor is used as the reactor.

23. The process for producing a butyric acid ester derivative according to claim 19, wherein R is ethyl or t-butyl.

24. The process for producing a butyric acid ester derivative according to claim 23 wherein R is ethyl.

25. The process for producing a butyric acid ester derivative according to claim 19, wherein X is chlorine atom or bromine atom.

26. The process for producing a butyric acid ester derivative according to claim 25 wherein X is chlorine atom.

27. The process for producing a butyric acid ester derivative according to claim 19, wherein the salt of prussic acid is sodium cyanide or potassium cyanide.

28. The process for producing a butyric acid ester derivative according to claim 27 wherein the salt of prussic acid is sodium cyanide.

29. The process for producing a butyric acid ester derivative according to claim 19, wherein each of the compound of the general formula (3) and the butyric acid ester derivative of the general formula (2) is an optically active compound.

30. The process for producing a butyric acid ester derivative according to claim 19, wherein the reaction is carried out in the presence of an addition reagent capable of adding itself to an ethylenic bond to convert a compound of the general formula (1)

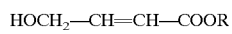

wherein R has the same meaning as defined above, to an addition product separable from the butyric acid ester derivative of the general formula (2)

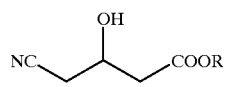

wherein R has the same meaning as defined above.

31. The process for producing a butyric acid ester derivative according to claim 30 wherein the addition product is a water-soluble compound.

32. The process for producing a butyric acid ester derivative according to claim 30 wherein the addition reagent is a salt of sulfurous acid.

33. The process for producing a butyric acid ester derivative according to claim 32 wherein the addition reagent is sodium sulfite or potassium sulfite.

* * * * *